United States Patent [19]

Abra et al.

[11] Patent Number: 4,766,046
[45] Date of Patent: Aug. 23, 1988

[54] STABILIZED LIPOSOME/AMPHOTERICIN COMPOSITION AND METHOD

[75] Inventors: Robert Abra; Francis C. Szoka, both of San Francisco, Calif.

[73] Assignee: Liposome Technology, Inc., Menlo Park, Calif.

[21] Appl. No.: 781,395

[22] Filed: Sep. 27, 1985

[51] Int. Cl.[4] .............................. A61K 9/42; A61J 5/00
[52] U.S. Cl. ................................... 424/450; 264/4.3; 264/4.6; 436/829; 514/31
[58] Field of Search ................... 264/4.3, 4.6; 436/829; 424/38, DIG. 7, 450; 514/31

[56] References Cited

U.S. PATENT DOCUMENTS 4,411,894  10/1983  Shrank et al. ..................... 514/221
4,529,561  7/1985   Hunt et al. ....................... 436/829 X

FOREIGN PATENT DOCUMENTS 2013609  8/1979  United Kingdom .

OTHER PUBLICATIONS

Mehta et al., Bichimica et Biophysica Acta 770: 230–234 (1984).
Tremblay et al., Antimicrobial Agents and Chemotherapy, 26(2): 170–173 (1984).
Remington, Pharmaceutical Sciences, Mack Pub., Easton, 1980, Chapter 78.
Olson et al., Biochimica et Biophysica Acta, 557: 9–23 (1979).
Crowe et al., Biochimica et Biophysica Acta, 769: 141–150 (1984).
Lopez–Berestein et al., J. Infec. Dis., 151(4): 704–710 (1985).
Graybill et al., J. Infec. Dis., 145(5): 748–752 (1982).
Lopez–Berestein et al., J. Infec. Dis., 150(2): 278–283 (1984).

Primary Examiner—Christine M. Nucker
Attorney, Agent, or Firm—Ciotti & Murashige, Irell & Manella

[57] ABSTRACT

A dehydrated liposome/amphotericin B composition which, upon addition of an aqueous medium, forms a suspension of liposomes (a) having a predetermined size distribution in size range less than about 1 micron, and (b) containing at least about 1 mole percent amphotericin B. The composition is prepared by forming a suspension of heterogeneous size amphotericin B liposomes in an aqueous solution containing at least about 0.5% of a membrane-stabilizing agent. The suspension is sized—for example, by extrusion through a small-pore polycarbonate membrane—to produce liposomes having the selected size distribution, and dehydrated.

4 Claims, No Drawings

STABILIZED LIPOSOME/AMPHOTERICIN COMPOSITION AND METHOD

FIELD OF THE INVENTION

The present invention relates to drug delivery by a liposome carrier, and in particular, to a stable liposome-/amphotericin B composition and method of forming same.

REFERENCES

The following references are referred to herein by corresponding number:
1. Holz, R. W., in F. E. Hahn, ed., Antibiotics, vol. 2, Springer-Verlag, N.Y. (1979).
2. Trembley, C., et al, Antimicrob Agents and Chemoth, 26(2):170 (1984).
3. Mehta, R. T., et al, Infection and Immunity, 47(2):429 (1985).
4. Lopez-Berestein, G., et al, Cancer Drug Delivery, 1(1):37 (1983).
5. New, R. R. C., et al, J Antimicrob Chemoth, 8:371 (1981).
6. Graybill, J. R., et al, J Infect Dis, 145:5 (1982).
7. Lopez-Berestein, G., J Infect Dis, 150(2):278 (1984).
8. Trembley, C., et al, Invest Opthalmol, 26:711 (1985).
9. Lopez-Berestein, G., et al, J Infect Dis, 151(4):704 (1985).
10. Juliano, R., et al, Biology of the Cell, 4(39) (1983).
11. Mehta, R., et al, Biochem Biophys Acta, 770:230 (1984).
12. Hopfer, R. L., et al, Antimicrob Agents and Chemoth, 25(3):387 (1984).
13. Szoka, F., Jr., et al, Ann Rev Biophys Bioeng, 9:467 (1980).
14. Szoka, F., Jr., et al, Proc Nat Acad Sci (USA), 75:4194 (1978).
15. Barza, M., et al, Proc and Abst of 23rd Interscience Conf on Antimicrob Agents (ICAAC). p. 133 (24 October 1983).
16. Norman, A. W., et al, Adv Lip Res, 14:127 (1976).

BACKGROUND OF THE INVENTION

Amphotericin B (AMB) is an effective antifungal agent, and at present, is the drug of choice for most serious fungal infections (reference 1). The drug binds strongly to ergosterol, a major sterol component of fungal membranes, forming pores in the membranes which allow leakage of solute molecules.

The drug also has a strong binding affinity for cholesterol, a sterol present in most mammalian cell membranes, and is therefore capable of disrupting host cells. When AMB is administered in free form, side effects resulting from red blood cell disruption are observed initially, followed by more serious cardiotoxicity effects. Renal toxicity, resulting from the body's attempt to clear the drug, is also present.

Several studies have shown that AMB toxicity can be reduced significantly by administering the drug in a liposome-bound form (references 2-12). Typically, the $LD_{50}$ of the drug increases from about 2-3 mg/kg body weight for the free drug up to about 8-15 mg/kg when the drug is administered in liposomal form. The decreased toxicity of liposome-associated AMB is presumably related to the ability of the liposomal membrane, and particularly sterol components in the membrane, to compete with host cell membrane for binding to the drug. Ergosterol, which has a higher affinity for AMB than cholesterol, shows a greater protective effect than cholesterol in liposomes (reference 12). However, cholesterol-containing liposomes allow more favorable AMB exchange between liposomes and the fungal target membranes, and are thus generally more beneficial as a carrier for therapeutic AMB.

For a variety of reasons, it is desirable that AMB liposomes which are used for therapeutic purposes have stable, sizes in a defined size range less than about 1 micron. Cholesterol-containing liposomes with sizes greater than about 1-2 microns are generally more toxic than smaller liposomes when administered parenterally, i.e., into the bloodstream. The toxicity of large liposomes in the bloodstream is related in part to liposome blockage of the alveolar capillaries. There are also indications that larger liposomes are more toxic to the liver, presumably due to accumulation of large liposomes in reticuloendothelial cells.

In addition to toxicity effects, liposome size may be an important determinant for in vivo drug release rates and liposome targeting. For example, where AMB liposomes are injected intramuscularly, the size of the liposomes may be an important variable in controlling either liposome migration and/or drug release from the site of injection. Liposomes have also been used in administering drugs by inhalation, as described in co-owned patent application for "Liposome Inhalation System and Method", Ser. No. 737,221, filed May 22, 1985. In this system, control of liposome sizes may be important in achieving reproducible drug delivery and/or drug release characteristics.

Heretofore, attempts to produce AMB liposomes having stable, selected sizes have not been successful. This is because AMB, like other polyene antibiotics, destabilizes liposome membranes, causing liposome fusion and general size increase over time. For example, AMB liposomes which have an initial average size less than about 1 micron typically show a 200-300% increase in average size after one month of storage at refrigerator temperature.

SUMMARY OF THE INVENTION

It is therefore one object of the invention to provide an AMB liposome composition which, after storage for an extended period, can be administered as a suspension of liposomes having a predetermined size distribution in a size range less than about 1 micron.

Another object of the invention is to provide a method for producing such a liposome composition.

A more general object of the invention is to provide a method of stabilizing the size distribution of liposomes which contain a lipophilic drug whose presence in the liposomal membrane promotes liposome fusion and size growth.

The invention includes a dehydrated lipid/AMB composition which, upon rehydration in an aqueous medium, forms a suspension of liposomes (a) having a predetermined size distribution in a size range less than about 1 micron, and (b) containing at least about 1 mole percent amphotericin B. The composition preferably contains cholesterol, at a mole ratio of between about 20-50% mole percent of the liposome membrane components and AMB, at a mole ratio of between about 3-7%. A membrane-stabilizing agent in the composition acts to stabilize the liposomes during dehydration and subsequent rehydration.

The method of the invention includes preparing a suspension of heterogeneous size liposomes containing at least about 1 mole percent AMB in the lipid phase and, in the aqueous phase, at least about 0.5% of a membrane-stabilizing agent. The liposome suspension is sized to produce a selected size distribution, then dehydrated. Rehydration of the lyophilized material, after an extended storage period, is effective to produce a liposome suspension in which the selected size distribution is substantially preserved.

In a more general aspect, the method is useful for size-stabilizing liposomes containing a lipophilic drug, such as AMB or other polyene antibiotic, which promotes liposome fusion.

These and other objects and features of the invention will become more fully apparent from the following detailed description of the invention.

DETAILED DESCRIPTION OF THE INVENTION

I. Stabilized AMB Liposomes

A. Liposome Preparation

The method of the invention involves, first, preparing a suspension of the heterogeneous size AMB liposomes containing AMB, at a lipid-phase concentration of a least 1 mole percent, and a membrane protective agent encapsulated within the liposomes. The liposomes are formed from standard phospholipid and sterol components, such as those listed on page 471 in reference 13. Preferred lipid components include phosphatidylcholine (PC), phosphatidylglycerol (PG), or other negatively charged phospholipid, and cholesterol or other related sterol, such as cholesterol hemisuccinate. The concentration of phospholipid components is preferably between about 55–80 mole percent. The sterol component is preferably present at a concentration between about 20–45 mole percent. It will be seen in Example VI that increasing amounts of cholesterol, up to at least about 20 mole percent, reduce the toxicity of AMB liposomes in mice. At an upper limit, the liposome bilayer can stably accommodate up to about 50 mole percent cholesterol. The lipids may also contain a lipothilic antioxidant, such as alpha-tocopherol ($\alpha$-T) or an $\alpha$-T analog. One preferred lipid composition, described generally in Example I below, includes PC, PG, cholesterol, and $\alpha$-T at mole ratios of 49.7:5.5:44.2:0.6.

The acyl chain composition of one or more of the phospholipid components may be selected to improve liposome sizing, size stability, and/or therapeutic characteristics. The effect of phospholipid acyl chain composition on size stability in liposomes, either before or after the dehydration procedure of the present invention, will be discussed below. In terms of AMB liposome toxicity, it will be seen in Example VI that AMB liposomes with saturated acyl chains are generally less toxic than liposomes with more unsaturated PC and PG components. The acyl chain composition may also be selected to achieve a selected drug release rate in vivo. As a rule, liposomes whose acyl chain components have higher transition temperatures are more stable in vivo, and therefore give slower rates of drug release. Phospholipids such as PC and PG having a variety of acyl chain lengths and/or degree of saturation are commercially available or can be prepared by standard procedures.

AMB is included in the liposomes at a mole ratio of at least about 1 mole percent, and preferably between about 3–7 mole percent, of the lipid components forming the liposomes. The preferred AMB concentration is typically the highest AMB mole ratio which allows liposomes to be prepared and sized in a selected size range. For example, one useful technique or producing liposomes having a relatively narrow size distribution is to extrude relatively large, heterogeneous size liposomes through a small-pore polycarbonate membrane (reference 14). Experiments conducted in support of the present invention indicate that liposome containing 3.5 mole percent AMB show good correspondence between liposome average size and membrane pore size, but that with higher AMB concentrations, the extruded liposomes tend to be somewhat larger than the membrane pore size.

The encapsulated membrane-stabilizing agent is a carbohydrate which functions to protect the liposomes from significant size changes on dehydration and rehydration. The experiments reported in Example V show that all of the mono and disaccharides tested—including glucose, mannitol, trehalose, sucrose, and lactose—give good size stabilization in liposomes containing 3.5 mole percent AMB. Maltodextrin (a mixture of higher molecular weight carbohydrates) provides size stabilization for liposomes containing 7 mole percent AMB, but not at lower AMB concentrations (5 and 3.5 mole percent). Lactose and trehalose were tested in liposomes containing 7 mole percent AMB, and both found to provide good size stabilization. Maltodextrin (a mixture of higher molecular weight polysaccharides) gives effective size stabilization in liposomes containing 7 mole percent AMB, but not at lower (5 and 3.5 mole percent) AMB concentrations (Table V below). Effective stabilizing agents can be identified readily by testing their ability to preserve a given liposome size distribution, after dehydration and rehydration, according to the procedure described generally in Example V.

A variety of methods are available for preparing liposome suspensions, as reviewed in reference 13. In one preferred method, a film of dried lipid/AMB film is hydrated with an aqueous buffer medium to produce a suspension of multilamellar vesicles (MLVs), with sizes ranging typically from less than 0.05 microns to more than 20 microns. Methods for preparing the lipid/AMB film are described in Examples I–III below. In one method, a dried film of the vesicle-forming lipids is taken up in a methanolic solution of AMB, which is then dried to form the lipid/AMB film (Example I). In a second method, dry AMB is added to a methanolic solution of lipids, and the mixture is dried as a film (Example II). A third method (Example III) is carried out by adding dry particulate-stabilizing agent (i.e., carbohydrate) to the methanolic solution of method 2. This mixture is then dried down to form a layer of lipid-coated carbohydrate particles which adhere to the bottom of the drying flask. This dried mixture hydrates more readily than the lipid films of the first two methods, and the resulting MLVs can be sized, by membrane extrusion, to sizes which are quite similar to the pore size of the extrusion membrane.

The aqueous medium used in hydrating the lipid film is preferably a physiologically compatible buffer, such as Tris—HCl, pH 7.4. The medium contains the membrane protective agent, at a preferred concentration of between 0.5 and 10% w/v, and the total solute concentration is preferably adjusted to about 290 mOsm (isotonic). The aqueous solution is added to the film and the lipids allowed to hydrate under either rapid (with shaking) or slow (without shaking) conditions. In general, the size distribution of MLVs in the above procedure can be shifted toward smaller sizes by hydrating the lipid film more rapidly, with shaking. The liposomes contain encapsulated membrane protective agent, at a concentration approximately equal to the bulk aqueous phase concentration.

B. Liposome Sizing

The liposome suspension is sized to achieve a selective size distribution of vesicles in a size range less than about 1 micron. The sizing serves to eliminate larger liposomes and to produce a defined size range having desired pharmacokinetic properties. Where sizing is used to reduce liposome sizes to about 0.4 microns or less, the liposome suspension may be readily sterilized by filtration through a conventional depth filter, such as a 0.22 micron depth filter composed of cellulose acetate and nitrate esters.

Several techniques are available for reducing the sizes and size heterogeneity of liposomes. Sonicating a liposome suspension either by bath or probe sonication produces a progressive size reduction down to small unilamellar vesicles (SUVs) less than about 0.05 micron in size. Homogenization is another method which relies on shearing energy to fragment large liposomes into smaller ones. In a typical homogenization procedure. MLVs are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution whose average is in the range between about 0.2 and 1 micron, depending on the pore size of the membrane. Typically, the suspension is cycled through the membrane several times until the desired size distribution is achieved. The liposomes may be extruded through successively smaller-pore membranes, to achieve a gradual reduction in liposome size. Alternatively, or in addition, the extrusion system can be operated at an elevated pressure, e.g., between 100–500 psi, to facilitate extrusion. The sizing procedure described in Example I involves extrusion 10 times each through a 0.4 and 0.2 micron filter. Liposomes prepared by this method showed the following size ranges, expressed as average size ± standard deviation, for the three AMB concentrations indicated in Table I.

TABLE I

| AMB (mole %) | Size ± S.D. (microns) |
|---|---|
| 3.5 | 296 ± 134 |
| 5.0 | 427 ± 218 |
| 7.0 | 376 ± 208 |

Centrifugation and molecular sieve chromatography are other methods which are available for producing a liposome suspension with particle sizes below a selected threshold less than 1 micron: These two methods both involve preferential removal of larger liposomes, rather than conversion of large particles to smaller ones. Liposome yields are correspondingly reduced.

The liposome suspension may be treated, either before or after sizing, to remove free (unbound) AMB from the suspension. Removing free drug is useful where free drug is found to interfere with the sizing procedure, and also minimizes the solution effects that the free drug might have on liposomes during dehydration and rehydration, for example, due to drug crystallization. Free drug and/or other unwanted solutes can be removed by ultrafiltration, followed by dilution with a suitable replacement medium. The method described in Example I employs an ultrafiltration step prior to liposome sizing, and in Example II, following liposome sizing. The concentration of liposome-associated AMB, after removal of free drug, is shown in Table II below for various initial AMB concentrations. Free AMB can also be removed from liposome suspensions by high speed contrifugation, resuspending the liposome pellet in a drug-free aqueous medium.

The liposome suspension should be sterilized after the above processing steps, and before dehydration. As indicated above, liposomes having sizes of about 0.4 microns or less can be sterilized by filtration through a conventional depth filter of the type used for removing bacterial contaminants. The dehydrated lipid/AMB composition of the invention can be sterilized by gamma radiation.

II. Therapeutic Uses

A. AMB Liposome Toxicity

This selection examines a number of factors which effect the toxicity of AMB liposomes in animals, and how the present invention contributes to reduced drug toxicity. The experiments referred to in this section are described generally in Example V.

One important factor in AMB liposome toxicity is the presence in the liposomes of a sterol, such as cholesterol, which is capable of binding to and sequestering AMB in the liposomal bilayer. The relationship between cholesterol concentration in AMB liposomes and toxicity was examined in liposomes containing 5 mole percent AMB, egg PC, egg PG, and increasing amounts of cholesterol, ranging from 0 to 44 mole percent, where the amount of PC was adjusted to compensate for cholesterol concentration. The experiment, which is reported in Table V, indicates a significant increase in $LD_{50}$ value between 0 and 22 mole percent cholesterol, and a further increase up to about 28 mole percent. No statistically significant change in toxicity was observed between about 28 and 44 mole percent cholesterol.

As mentioned above, the acyl chain composition of liposomal lipids can be important in regulating the stability and, therefore, the drug release rates of liposomes. For this reason, it was of interest to determine if acyl chain composition also significantly effects the drug toxicity of AMB liposomes. The study reported in Example V compared the animal toxicity of liposomes whose phospholipid components were either (a) egg PC and egg PG, (b) dimyristoyl PC (DMPC) and DMPG, or (c) dipalmitoyl PC (DPPC) and DPPG. The fatty acyl group(s) of egg phospholipids are 16:0 (42%), 18:1 (28%, and 18:2 (16%); of dimyristoyl phospholipids, 14:0; and of dipalmitoyl phospholipids, 18:0. The $LD_{50}$ data given in Table VI suggests that liposomes composed of saturated-chain PC and PG (either dimyristoyl or dipalmitoyl) are less toxic than AMB liposomes composed of egg phospholipid components.

An important aspect of the present invention is the ability to control liposome sizes, over an extended storage period, within a defined size range less than about 1 micron. One potential advantage of controlling size growth is reduction in toxicity, in view of the generally greater toxicity of cholesterol-containing AMB liposomes having sizes larger than about 0.8 microns (reference 15). The data shown for composition 3 in Table VII below, showing much higher toxicity for 2.5 micron size liposomes compared with 0.4 micron liposomes, confirm that size exerts a significant influence on toxicity of AMB liposomes. That the liposome suspensions in Table VII which have average sizes between 0.5 and 0.8 micron show comparatively low toxicity (high $LD_{50}$ values) indicates that the size-toxicity effect is less significant below about 1 micron.

Three of the liposome compositions listed in Table VI were tested for animal toxicity both before and after lyophilization and rehydration. In all cases, the toxicity after rehydration was nearly the same as that before lyophilization. The results are consistent with the liposome size data, which show that the sizes of the liposomes are substantially stable after dehydration and rehydration.

In fact, decreases in average liposome size between about 37-50% were observed, the size of decrease being well within the standard deviation of sizes. The data in Table II indicate that increases or decreases in liposome size of up to about 50%, after dehydration/rehydration, are characteristic of the method of the invention, and may be related to the concentration of both AMB and the protective agent. For purposes of definition, the size distribution of the liposomes is considered substantially preserved. The average liposome size after dehydration/rehydration is within about 50% of the original average liposome size.

B. Drug Delivery Modes

AMB liposomes are useful in treating a variety of systemic fungal organisms. The efficacy of AMB liposome compositions against candidiasis (references 2, 4, 7, 9, and 12), histoplasmosis (reference 15), cryptococcosis (reference 6), and leishmaniasis (reference 5) in model animal systems has been well established. Heretofore, due to the size instability of AMB liposomes, it has not been possible to prepare and store small-diameter AMB liposomes without a significant (severalfold) size increase over a several week storage period. As a result, due to different in vivo liposome uptake and drug release and toxicity properties which are related to liposome size, it has been difficult to control and evaluate the therapeutic index of stored AMB liposomes. The size instability problem is particularly serious where liposome sizes greater than 1-2 microns are attained, since cholesterol-containing AMB liposomes are substantially more toxic than the smaller, original size liposomes. The size stability problem has been solved heretofore only by administering the sized liposomes shortly after preparation. This, of course, is an impractical approach to drug delivery in the usual clinical setting.

The present invention provides a dehydrated lipid/AMB composition which, when rehydrated after an extended storage period, forms a suspension of liposomes having a selected size range less than about 1 micron. Further, because the liposomes can be stored in an anhydrous, inert environment, toxicity and liposomal breakdown problems related to oxidation and mechanical damage at a gas/liquid interface are minimized. For parenteral use, e.g., intravenous administration, the composition is preferably formed from AMB liposomes having sizes of between about 0.1 to 0.4 microns, such as can be prepared by membrane extrusion. The size distribution is preferably selected, on an empirical basis, to achieve, in addition to low toxicity, (a) optimal uptake in the tissue region of interest, and/or (b) optimal drug release kinetics. The AMB/lipid composition is hydrated typically to a selected concentration of between about 20 and 200 $\mu$mole total lipid/ml, and administered at a concentration of between 1 and 5 mg AMB/kg body weight.

Where the drug is given intramuscularly, to provide slow drug release from the site of injection, the composition is preferably rehydrated to a more concentrated form, which can be conveniently localized at an injection site. The size distribution is selected for reduced toxicity, and desired kinetics of liposome or drug release from the site of injection. For example, there is evidence that small unilamellar vesicles (SUVs) can migrate readily from an intramuscular site, wherein the rate of drug release into the bloodstream would be determined both by liposome migration into and stability in the bloodstream. By contrast, drug release characteristics of larger liposomes, which tend to remain at the site of injection, would be dependent on liposome stability and density at the site of injection. In either case, it is advantageous that the injected liposomes have a predictable, selected size distribution.

For drug delivery by inhalation, the optimal size composition and concentration of rehydrated suspension will be governed by the approach used for atomizing the suspension, and the desired vapor droplet size. Co-owned patent application for "Liposome Inhalation Method and System", cited above, discusses these factors.

The following examples illustrate various AMB/lipid compositions, methods of forming the compositions, and size and in vivo toxicity characteristics of the rehydrated AMB liposomes. The examples are intended to illustrate, but not limit, the scope of the invention.

Materials

Amphotericin B was supplied by the Squibb Institute for Medical Research (Princeton, NJ); phospholipids, at greater than 99% purity, from Avanti Polar Lipids (Birmingham, AL); cholesterol and $\alpha$-tocopherol, both chromatographic grade, from Sigma Chemical Co. (St. Louis, MO), trehalose, from Pfanstiehl Labs, Inc. (Waukegan, IL); lactose and mannitol, from Sigma; and maltodextrin, from E. T. Horn (Oakland, CA). All other chemicals were reagent grade or better. Phosphate buffered saline (PBS) contained 6.4 mM disodium hydrogen phosphate, 2.6 mM KCl, and 154 mM NaCl, pH 7.4, 290 milliosmoles (mOsm).

EXAMPLE I

Preparation of AMB Liposomes

Method 1

Each of three lipid mixtures containing a phosphatidylcholine (PC), a phosphatidylglycerol (PG), cholesterol (CH), and $\alpha$-tocopherol ($\alpha$-T), at a mole ratio of 49.7:5.5:44.2:0.6, was prepared by combining the lipids, in suitable solvents, in a round-bottom flask, and drying the solvent mixture to form a lipid film. Mixture #1 was prepared with egg PC (EPG) and egg PG (EPG); mixture #2, with dimyristoyl PC (DMPC) and dimyristoyl PG (DMPG); and mixture #3, with dipalmitoyl PC (DMPC) and dipalmitoyl PG (DMPG).

Amphotericin B (AMB), prepared as a methanolic solution containing about 100 $\mu$g AMB/ml, was added to the lipid film in the flask to a final concentration of either 3.5, 5.0, or 7.0 mole percent AMB. The AMB solution was added in up to three separate aliquots, and after each aliquot addition, the flask was swirled to suspend or dissolve all of the dried lipids in the flask, then dried in vacuo to reform a lipid film in the flask.

After the final addition of AMB, the dried lipid-/AMB film was hydrated with about 10-20 ml of a selected aqueous medium, specified below, with gentle shaking in the presence of glass beads for 1 hour at either room temperature, for mixtures #1 and #2, or at 45° C., for mixture #3. The liposomes which formed were multilamellar vesicles (MLVs) having heterogeneous sizes up to about 20 microns. The MLV suspension were sized by extrusion through a polycarbonate membrane, substantially according to the method of reference 14, but at an extrusion pressure of about 100-500 psi lipid on lipid. The extrusion device was supplied by Webb Scientific Co. (Vancouver, B.C.). Typically, the suspension was passed ten times through a 0.4 micron filter, then 10 times through a 0.2 micron filter, both obtained from BioRad (Richmond, CA).

The extruded suspension was diluted fivefold with a selected buffer, then concentrated to its original volume in an ultrafiltration cell containing a 300,000 mw cut-off Diaflow membrane obtained from Amicon (Danvers, MA). The dilution/concentration step removed most of the free AMB from the suspension. The final concentrations of liposome-bound AMB in a suspension of MLVs prepared with lipid mixture #1, at 3.5, 5.0, or 7.5 mole percent AMB, are shown in Table I. AMB was assayed spectrophotometrically at 406 nm.

TABLE II

| AMB (mole %) | Aqueous Medium | Liposomal AMB $\mu$AMB/$\mu$mole lipid |
|---|---|---|
| 3.5 | 10 mM Tris-HCl, 5% lactose w/v | 13 |
| 5.0 | 10 mM Tris-HCl, 5% lactose w/v | 23 |
| 7.0 | PBS | 63 |

EXAMPLE II

Preparation of AMB Liposomes

Method 2

In this procedure, lipid film formed in Example I was taken up in a methanolic solution and dry AMB was added to the solution to a final concentration of 100 $\mu$g AMB/ml methanol and 3.5, 5.0, or 7.0 mole percent AMB of total lipid, and the mixture was swirled until completely dissolved. After drying the mixture to a thin film in vacuo, an aqueous medium was added, with gentle shaking in the presence of glass beads, to form a suspension of AMB-containing MLVs, as in Example I.

The suspension was diluted 5-fold with buffer, concentrated to the original suspension volume by ultrafiltration to remove free AMB, then extruded ten times each through a 0.4 micron membrane, and a 0.2 micron membrane. The ultrafiltration and extrusion steps were performed as in Example I.

EXAMPLE III

Preparation of AMB Liposomes

Method 3

A methanolic solution of vesicle-forming lipids and 5 mole percent AMB was formed as in Example II. To the solution was added dry powdered lactose, in an amount calculated to produce a 5% lactose solution in the final liposome suspension. The mixture was dried under vacuum in a round-bottom flask, yielding a powder of lactose particles coated with lipids and AMB adhering to the sides of the flask.

The lipid/lactose particles were hydrated in 10 mM Tris—HCl, pH 7.4, with gentle shaking. The lipid material readily hydrated without using glass beads and no yellow lipid residue remained on the side of the flask, in contrast to the hydration procedure in Examples I and II, where lipid hydration was incomplete, even when glass beads were used to disrupt the lipid film.

The MLVs which formed were diluted, concentrated by ultrafiltration, and extruded successively through 0.4 and 0.2 micron polycarbonate membranes, as in Example II. The sized vesicles had an average pore size of 250±113 nm (as determined below in Example IV). After lyophilization and rehydration, the average size was 221±194 nm.

EXAMPLE IV

Time-Dependent Increase in Liposome Size

AMB-containing liposomes were prepared from lipid mixture #1 (Example 1) and 7 mole percent AMB in PBS according to the procedure described in Example I. Immediately after the extrusion and the dilution/concentration steps, the size distribution of liposomes in the suspension was measured by Laser Particle Sizer (Nicomp Instruments Inc., Santa Barbara, CA), calibrated with 1 micron latex beads.

The suspension was stored at 4° C. for 35 days under nitrogen. At the various times indicated below in Table II, aliquots of the suspension were withdrawn and examined for liposome size distribution. The results are shown in the right-hand column in the table. As seen, the average and largest sizes of liposomes increased 2-3-fold over the 35-day storage period.

TABLE III

| Days Storage | Size (Mean ± S.D. in nm) |
|---|---|
| 0 | 376 ± 208 |
| 1 | 407 ± 231 |
| 12 | 662 ± 302 |
| 20 | 853 ± 485 |
| 28 | 949 ± 527 |
| 35 | 884 ± 494 |

Similar patterns of liposome size increase were noted for liposomes prepared with lipid mixtures #2 and #3, at 7% AMB, for AMB liposomes prepared to contain 5% w/v lactose or 5% w/v maltodextrin, and for AMB liposomes prepared with a Tris—HCl buffer, rather than PBS at 5 and 3.5 mole percent AMB. A control liposome suspension prepared without AMB showed substantially no size change over the 35-day-storage period.

EXAMPLE V

Effect of Membrane Protective Agent on Liposome Size

Liposomes were prepared from mixture #1 lipids and 3.5 mole percent AMB, with hydration in either PBS, or in a Tris—HCl buffer containing 5% w/v of one of the following sugars: glucose, mannitol, trehalose, sucrose, lactose, or maltodextrin. The MLVs formed on hydration with the selected aqueous medium were extruded successively through 0.4 and 0.2 micron polycarbonate membranes, diluted with the selected medium, and concentrated to the original volume, according to Example I. The liposome suspensions were frozen against a dry ice/isopropanol mixture and lyophilized at a pressure of about 15 mTorr. The lyophilized material was stored under nitrogen at refrigerator temperature until used, typically at least about 12 hours.

Following storage, each of the lyophilized liposome preparations was resuspended to its prelyophilization volume by addition of distilled water. The samples were agitated briefly to facilitate resuspension, and resuspended samples were examined for liposome size distribution, as above. Table IV below compares the size distribution of the liposomes following lyophilization and resuspension, with that observed for liposomes immediately after initial preparation, i.e., before freezing and lyophilization.

TABLE IV

| AMB (mole %) | Hydration Medium | Size Increase (Mean ± S.D. in nm) | |
|---|---|---|---|
| | | initial | rehydrated |
| 3.5 | 5% w/v glucose | 362 ± 175 | 267 ± 123 |
| 3.5 | 5% w/v mannitol | 383 ± 189 | 348 ± 169 |
| 3.5 | 5% w/v trehalose | 448 ± 218 | 360 ± 175 |
| 3.5 | 5% w/v sucrose | 337 ± 158 | 305 ± 138 |
| 3.5 | 5% w/v lactose | 444 ± 211 | 331 ± 151 |
| 3.5 | 5% w/v maltodextrin | 397 ± 181 | 995 ± 530 |

As seen, each of the mono and disaccharides tested was effective in stabilizing liposome size on dehydration and rehydration. By contrast, AMB vesicles prepared in the presence of maltodextrin showed the same 2–3 fold increase in size, following dehydration and rehydration, that was observed for liposomes prepared in PBS (no membrane-stabilizing agent present).

Table V below shows the size-stabilizing effect of mannitol, lactose, trehalose, and maltodextrin at varying sugar and AMB concentrations. At higher AMB concentrations, both lactose and trehalose were effective membrane stabilizers, as was maltodextrin, but mannitol was not. In agreement with the data in Table IV, maltodextrin was ineffective at 3 mole percent AMB, and also at 5 mole percent.

TABLE V

| AMB (mole %) | Hydration Medium | Size Increase (Mean ± S.D. in nm) | |
|---|---|---|---|
| | | initial | rehydrated |
| 7.0 | PBS | 1184 ± 606 | 3969 ± 1153 |
| 7.0 | 5% mannitol | 848 ± 464 | 2036 ± 1153 |
| 7.0 | 0.5% lactose | 448 ± 239 | 629 ± 352 |
| 7.0 | 5% lactose | 876 ± 473 | 629 ± 339 |
| 7.0 | 0.5% MD | 305 ± 157 | 515 ± 283 |
| 7.0 | 5% MD | 796 ± 439 | 805 ± 454 |
| 7.0 | 10% trehalose | 603 ± 319 | 780 ± 470 |
| 5.0 | 5% lactose | 427 ± 218 | 337 ± 166 |
| 5.0 | 5% MD | 1075 ± 617 | 2443 ± 1331 |
| 3.5 | 5% lactose | 296 ± 134 | 288 ± 128 |
| 3.5 | 5% MD | 1080 ± 612 | 5387 ± 3 |

EXAMPLE VI

The toxicity of AMB liposomes as a function of cholesterol concentration, liposome size, and liposome acyl chain composition was examined. In a first experiment, liposome suspensions containing egg PC (from 93.9 to 49.4 mole percent) and α-T (0.6 mole percent) were prepared substantially as in Example II. The suspensions are identified by mole percent cholesterol at the left in Table V below. Each of the suspensions was sized by extrusion, as described in Example I, yielding the liposome size distributions shown in the second column of the table. The size measurements were made after lyophilization and rehydration, except for the first-row sample, which was measured before lyophilization.

Female Swiss-Webster mice, obtained from Simonson (Gilroy, CA) were divided into groups of 5–10 mice each. Each group was given intravenous injections of one of the six liposome compositions shown in Table VI, at AMB dosages of between about 5–22 mg/kg animal body weight. The total number of animals injected, for each liposome composition is indicated in the table. Survival was determined after 5 days. As seen, higher cholesterol concentrations in the liposomes generally correlate with higher $LD_{50}$ values, i.e., with lower drug toxicity.

TABLE VI

| % Cholesterol | Size ± S.D. (nm) | No. Animals | $LD_{50}$ (mg/kg) |
|---|---|---|---|
| 44.2 (PL) | 450 ± 213 | 23 | 8.9 ± 1.7 |
| 44.2 | 283 ± 129 | 24 | 6.6 ± 2.0 |
| 33 | 331 ± 148 | 53 | 5–10 |
| 28 | 288 ± 138 | 12 | 8 |
| 22 | 306 ± 156 | 12 | <8 |
| 0 | 264 ± 123 | 12 | <<8 |

Similar $LD_{50}$ studies were performed with AMB liposomes having the lipid compositions shown at the left in Table VII below. These liposomes were also prepared as in Example II. The compositions were formed with 3.5 mole percent AMB, except for composition #2, which contained 1 mole percent AMB, and composition #3, which contained 10 mole percent AMB. Sizing was done by extrusion, according to Example I, with the results shown in the second column in the table. $LD_{50}$ studies were performed as above, using female Swiss-Webster mice injected intravenously. The number of animals injected with each composition is indicated in the table.

TABLE VII

| Composition | Size ± S.D. (μnm) | No. Animals | $LD_{50}$ (μg/Kg) |
|---|---|---|---|
| 1. EPC/EPG/CH/α-T | 450 ± 213 | 23 | 8.9 ± 1.8 |
| (49.4:5.5:44.2:0.6)(PL) | 283 ± 129 | 24 | 6.6 ± 2.0 |
| 2. DMPC/DMPG | — | 14 | <<8 |
| (9:1) | | | |
| 3. EPC/CH/α-T | | | |
| (5:4:0.1)(MLV) | 2452 ± 1228 | 18 | <<9 |
| (sonicated) | 338 ± 198 | 18 | 9 |
| 4. DPPC/DPPG/CH/α-T | 843 ± 431 | 13 | >12 |
| (49.7:5.5:44.2:0.6)(PL) | 416 ± 199 | 13 | >12 |
| 5. DMPC/DMPG/CH/α-T | 651 ± 328 | 13 | <12 |
| (49.7:5.5:44.2:0.6)(PL) | 397 ± 200 | 13 | >12 |
| 6. AMB/DOC | | | |
| Sigma | | 52 | 3.7 ± 0.1 |
| Squibb | | 44 | 3.2 |

From $LD_{50}$ values given in the table, the following general conclusions can be drawn: (1) the $LD_{50}$ value of the AMB liposomes varies with acyl chain composition, with highest $LD_{50}$ values being observed for unsaturated chain phospholipids (compositions 4 and 5); (2) cholesterol-containing AMB liposomes with sizes greater than about 2 microns are much more toxic than relatively small ones (composition 3 data); and (3) the presence of cholesterol substantially decreases the toxicity of AMB liposomes, supporting the data from Table VI.

There is claimed:

1. A method of administering liposomes containing between about 3 to 7 mole percent amphotericin B and having, after a storage period, a selected liposome size distribution in a size range between about 0.2 to 0.5 micron, comprising
    preparing a suspension of heterogeneously sized liposomes containing between about 3 to 7 mole percent amphotericin B in the lipid phase, and, in the aqueous phase, at least about 0.5% w/v of a membrane-stabilizing agent,
    reducing the size heterogeneity of the liposome suspension to achieve said selected liposome size distribution,
    lyophilizing the liposome suspension before the size distribution of the liposomes changes substantially,
    after such storage period, adding an aqueous medium to the lyophilized suspension, said adding being effective to produce a reconstituted suspension of liposomes in which the size distribution achieved by said reducing is substantially preserved, and administering the reconstituted liposomes before the size distribution of the liposomes changes substantially.

2. The method of claim 1, wherein the liposomes have a lipid composition which includes about 50–80 mole percent unsaturated phospholipids, and between about 20–50 mole percent cholesterol.

3. The method of claim 1, wherein the membrane-stabilizing agent includes at least about 0.5% w/v of an agent selected from the group consisting of glucose, mannitol, trehalose, sucrose, and lactose, when the amphotericin B concentration is less than about 4 mole percent, and about 0.5% w/v maltodextrin, when the amphotericin B concentration is greater than about 6 mole percent.

4. The method of claim 3, wherein the liposomes contain between about 6–7 mole percent amphoteracin B, and the membrane stabilizing agent includes about 0.5% w/v maltodextrin.

* * * * *